(12) United States Patent
Wang et al.

(10) Patent No.: US 9,273,127 B2
(45) Date of Patent: Mar. 1, 2016

(54) P28GANK MONOCLONAL ANTIBODY AND PEPTIDES FOR PREPARATION THEREOF AND USE THEREOF

(75) Inventors: Hongyang Wang, Shanghai (CN); Yao Chen, Shanghai (CN); Jing Fu, Shanghai (CN); Dongping Hu, Shanghai (CN); Tao Luo, Shangai (CN); Liwei Dong, Shanghai (CN)

(73) Assignee: The Second Military Medical University, The People's Liberation Army, Yangpu District, Shanghai (CN)

( * ) Notice: Subject to any disclaimer, the term of this patent is extended or adjusted under 35 U.S.C. 154(b) by 222 days.

(21) Appl. No.: 13/993,542

(22) PCT Filed: Dec. 9, 2011

(86) PCT No.: PCT/CN2011/083760
§ 371 (c)(1),
(2), (4) Date: Aug. 23, 2013

(87) PCT Pub. No.: WO2012/079488
PCT Pub. Date: Jun. 21, 2012

(65) Prior Publication Data
US 2013/0337467 A1 Dec. 19, 2013

(30) Foreign Application Priority Data
Dec. 13, 2010 (CN) .......................... 2010 1 0585000

(51) Int. Cl.
*C07K 1/00* (2006.01)
*C07K 14/00* (2006.01)
*C07K 14/435* (2006.01)
*C07K 14/775* (2006.01)
*C07K 16/00* (2006.01)
*C07K 16/18* (2006.01)
*C07K 16/30* (2006.01)
*G01N 33/574* (2006.01)

(52) U.S. Cl.
CPC ............... *C07K 16/18* (2013.01); *C07K 14/775* (2013.01); *C07K 16/303* (2013.01); *G01N 33/5748* (2013.01); *G01N 33/57438* (2013.01); *C07K 2317/34* (2013.01); *G01N 2333/82* (2013.01)

(58) Field of Classification Search
CPC ........ C07K 1/00; C07K 14/00; C07K 14/435; C07K 14/775; C07K 16/00; C07K 16/18; C07K 16/30; C07K 16/303; C07K 2316/00; C07K 2317/00; C07K 2317/34; G01N 203/00; G01N 2333/00; G01N 2333/435; G01N 2333/76; G01N 2333/775; G01N 2333/81; G01N 2333/82; G01N 33/574; G01N 33/57407; G01N 33/57438; G01N 33/5748
See application file for complete search history.

(56) References Cited

U.S. PATENT DOCUMENTS 7,833,988 B2    11/2010  Fujita
2005/0170424 A1 *  8/2005  Fujita ................................ 435/6

FOREIGN PATENT DOCUMENTS

CN          1513876 A       7/2004

OTHER PUBLICATIONS

Fu et al. A novel diagnostic marker, p28GANK distinguishes hepatocellular carcinoma from potential mimics. J Cancer Res Clin Oncol. 130: 514-520, 2004.*
Qin et al. Gene and protein expressions of p28GANK in rat with liver regeneration. World J Gastroenterol. 9(11):2523-2527, Nov. 2003.*
Umemura, Atsushi, et al., Association of Gankyrin Protein Expression with Early Clinical Stages and Insulin-Like Growth Factor-Binding Protein 5 Expression in Human Hepatocellular Carcinoma, Hepatology 2008, vol. 47, pp. 493-502.
International Search Report dated Mar. 22, 2012 for International Application Serial No. PCT/CN2011/083760, International Filing Date: Dec. 9, 2011 consisting of 4 pages.
Tao, Tao et al., Preparation and Identification of Monoclonal Antibodies Ggainst PSMD10, Journal of Tropical Medicine, vol. 6 No. 6 Jun. 2006, 4 pages.

* cited by examiner

*Primary Examiner* — Alana Harris Dent
(74) *Attorney, Agent, or Firm* — Christopher & Weisberg, P.A.

(57) ABSTRACT

The invention provides the sequences of two polypeptides comprising the amino acid sequences as shown in SEQ ID NO:1 and SEQ ID NO:2, which can be used for the preparation of monoclonal antibodies against human $p28^{GANK}$. The invention also provides the monoclonal antibodies against human $p28^{GANK}$ and their use.

5 Claims, 2 Drawing Sheets

A

B

P28GANK MONOCLONAL ANTIBODY AND PEPTIDES FOR PREPARATION THEREOF AND USE THEREOF

CROSS-REFERENCE TO RELATED APPLICATIONS

This application is a Submission Under 35 U.S.C. §371 for U.S. National Stage Patent Application of, and claims priority to, International Application Number: PCT/CN2011/083760, filed Dec. 9, 2011 entitled "P28$^{GANK}$ MONOCLONAL ANTIBODY AND PEPTIDES FOR PREPARATION THEREOF AND USE THEREOF," which claims priority to Chinese Patent Application Serial Number: CN 201010585000.4, filed Dec. 13, 2010, the entirety of both which are incorporated herein by reference.

TECHNICAL FIELD

The present invention relates to the field of biomedical engineering, i.e. relates to a monoclonal antibody against p28$^{GANK}$, the polypeptide used to prepare this monoclonal antibody against p28$^{GANK}$, and the use of the monoclonal antibody against p28$^{GANK}$ in the preparation of a reagent for hepatocarcinoma prognosis.

BACKGROUND OF THE INVENTION

P28$^{GANK}$ exists in human hepatocytes. Generally, P28$^{GANK}$ is over-express in HCC compared with normal liver tissues. The coding frame of p28$^{GANK}$ contains 226 amino acids with 6 repeating ankyrin sequence (Gene ID: 5716), and molecular weight is 25 kDa. The inventor has prepared a rabbit-anti-human polyclonal antibody against p28$^{GANK}$ useful for pathological diagnosis of hepatocarcinoma. The polyclonal antibody has been disclosed in the Chinese patent ZL03116825.6, the title of which is "Antibody against p28 for the differentiation and diagnosis of hepatocarcinoma and its preparation".

P28$^{GANK}$ has been reported to promote tumor progression mainly through the regulation of endoplasmic reticulum stress (ER stress), NF-κB, P53 and Rb signal pathways. P28$^{GANK}$ directly binds to RelA/NF-κB to accelerate the nuclear-export of NK-κB; p28$^{GANK}$ can bind to ubiqutin ligase MDM2 to mediate the ubiquitination-degradation of p53; p28$^{GANK}$ can bind to tumor-suppression protein Rb and drive the phosphorylation inactivation of Rb and the releasing of the nuclear transcription factor E2F-1, thus accelerate the cell cycle (See: Li H, et al. Use of adenovirus delivered siRNA to target oncoprotein p28GANK in hepatocarcinoma. Gastroenterology 2005; 128:2029-2041; Dai R Y, et al. p28GANK inhibits endoplasmic reticulum stress-induced cell death via enhancement of the endoplasmic reticulum adaptive capacity. Cell Research 2009 November; 19(11): 1243-1257 Chen Y, et al. Oncoprotein p28 GANK binds to RelA and retains NF-kappaB in the cytoplasm through nuclear export. 2007 December; 17(12): 1020-9).

It has been reported that the main factors affecting the prognosis of hepatocarcinoma were the tumor size and the vascular invasion, and usually accompanied by its multiple feature. At present, more and more researches show that the prediction of the recurrence of hepatocarcinoma still needs more effective prognostic factors. Previous researches show that p28$^{GANK}$ possibly play an important role in hepatocarcinoma progression, but the regulation mechanism of p28$^{GANK}$ is still unclear. Up to now, there isn't any report discloses that the expression level of p28$^{GANK}$ can be directly used as a prognostic factor for hepatocarcinoma recurrence and metastasis, as well as individual treatment index for hepatocarcinoma patients.

DESCRIPTION OF THE INVENTION

The present application is being filed with a Sequence Listing as a text file, in computer readable form, via EFS-Web. The Sequence Listing is provided as a file entitled 1777-3PUS_Sequence_Listing.txt created on Jun. 11, 2013, which is 929 bytes in size. The information in computer readable form is incorporated herein by reference in its entirety.

The purpose of the present invention is to provide the sequences of two polypeptides used for the preparation monoclonal antibodies against p28$^{GANK}$, and the monoclonal antibodies against p28$^{GANK}$. The monoclonal antibodies are used to preparation reagents for the hepatocarcinoma prognosis.

Given high expression of the p28$^{GANK}$ in hepatocarcinoma, the inventor studied the regulation of p28$^{GANK}$ in hepatocarcinoma metastasis. The experiments show that p28$^{GANK}$ can regulate PI3K-AKT-HIF1a pathway to promote hepatocarcinoma metastasis. P28$^{GANK}$ overexpression in hepatocarcinoma predicts a poor prognosis. So the monoclonal antibody specific recognizing p28$^{GANK}$ can be used to detect endogenous p28$^{GANK}$ in hepatocarcinoma patient biopsies and predict the prognosis for the patients. Thus, if the monoclonal antibody of p28$^{GANK}$ could block its tumor-promoting role, it will be possibly used for personalized treatment of these patients with high p28$^{GANK}$. Therefore, the monoclonal antibody against p28$^{GANK}$ can be used for the prognosis and individual treatment of hepatocarcinoma.

The present invention provides two polypeptide sequences which can be used for the preparation of monoclonal antibodies against human p28$^{GANK}$. The present invention also provides the monoclonal antibodies against human p28$^{GANK}$. The present invention also provides the use of the monoclonal antibodies against human p28$^{GANK}$.

The technical solutions are as follow:

1. The present invention provides two polypeptides comprising the amino acid sequences as shown in SEQ ID NO:1 and SEQ ID NO:2, which can be used for the preparation of monoclonal antibodies against human p28$^{GANK}$:

```
                              (SEQ ID NO: 1)
          NPDAKDHYEATAMHRC (SEQ ID NO: 2)
          CDEERVEEAKLLVSQ.
```

2. According the above-mentioned sequence, the inventor synthesized the two polypeptides respectively; which were used to prepare the p28$^{GANK}$ monoclonal antibodies.

3. The monoclonal antibodies of the present invention are secreted by hybridoma cell strains having CCTCC Deposit No: C201153 or CCTCC Deposit No: C201154.

4. The two hybridoma cell strains of this invention have Deposit number of CCTCC No: C201153 or CCTCC No: C201154, respectively.

5. The synthetic polypeptides, monoclonal antibodies and hybridoma cell strains of the present invention can be used to prepare the reagents or kits of immuno-histochemistry test; said reagent or kits of immuno-histochemistry test is used to detect the hepatocarcinoma and predict the prognosis for the patients.

The present invention provides the following method for preparing the mouse-anti-human p28$^{GANK}$ monoclonal antibodies:

1. synthesize two polypeptides according to the whole amino acid sequence of the coding frame of p28$^{GANK}$:

```
polypeptide No.1:
131-145,
NPDAKDHYEATAMHRC polypeptide No. 2:
180-194,
CDEERVEEAKLLVSQ;
```

2. couple the above-mentioned polypeptide with keyhole limpet hemocyanin (KLH) to produce an immunogen, which is used to immunize mice;

3. obtain the spleen cells of the immunized mice, and fuse the spleen cells with mouse myeloma cells;

4. obtain positive cell clones which can react with the synthesized polypeptide through multiple rounds of screening, said cell clones are used as hybridoma cell strains which can secrete the monoclonal antibodies against human p28$^{GANK}$;

5. inoculate a hybridoma cell strain to the mice and obtain the ascite (including antibody), purify the ascite to obtain the monoclonal antibody against human p28$^{GANK}$.

The present invention provides monoclonal antibodies against human p28$^{GANK}$ secreted by CCTCC Deposit No: C201153 and CCTCC Deposit No: C201154, recognizing the antigen epitopes NPDAKDHYEATAMHRC (SEQ ID NO: 1) and CDEERVEEAKLLVSQ (SEQ ID NO: 2) respectively.

The polypeptides of the invention can be synthesized by polypeptide synthesizer, the polypeptide fragment can be coupled with the carrier proteins such as KLH by glutaraldehyde linking method to produce an immunogen, which was used to immunize mice and screen the monoclonal antibodies.

The hybridoma cell strains secreting monoclonal antibodies against human p28$^{GANK}$ can be prepared by conventional technique in the art. For example, fuse the spleen cells of the immunized mice with mouse myeloma cells such as SP2/0 cells to obtain the hybridoma cells via screening process.

The monoclonal antibodies can be prepared by conventional technique in the art, i.e. inoculate the hybridoma cells to the mice and obtain the ascite (including antibody), purify the ascite to obtain the monoclonal antibody against human p28$^{GANK}$ to obtain the monoclonal antibodies.

The hybridoma cell strains of the present invention, also known as the hybridoma cell strains 160CT8531 (i.e. deposited in the China Center for Type Culture Collection, Deposit date: Sep. 21, 2011; Deposit number: CCTCC No: C201153) and 161CT7112 (i.e. deposited in the China Center for Type Culture Collection, Deposit date: Sep. 21, 2011; Deposit number: CCTCC No: C201154). The monoclonal antibodies secreted by such hybridoma cell strains are immunoglobulins which can specifically bind to human p28$^{GANK}$ protein.

The present invention also provides the use of the above-mentioned polypeptides, the monoclonal antibodies against human p28$^{GANK}$ and hybridoma cell strains in the prognosis assessment of the patients with liver diseases, specifically provides their use in the preparation of the reagents or kit of Western Blot or immuno-histochemistry test.

The present invention provides a new idea of p28$^{GANK}$ used for clinical personalized treatment.

Figure 1:
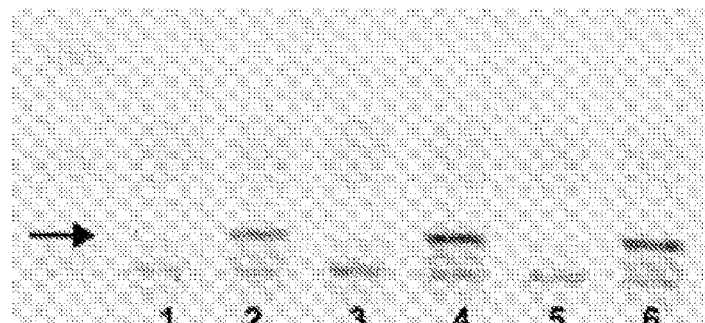
FIG. 1 shows the result of an experiment in which p28$^{GANK}$ proteins from the total cell lysates of cell lines SMMC-7721 (lane 1,3,5) and SMMC-7721-p28$^{GANK}$ containing exogenous transfected myc-p28$^{GANK}$ gene were detected by a Western Blot method using anti-p28$^{GANK}$ monoclonal antibodies. As a result, the expression of p28$^{GANK}$ was confirmed in above cell lines. "→" denotes the exogenous p28$^{GANK}$.

China Center for Type Culture Collection
Life Science College of Wuhan university, Luojia Hill, Wuchang, Wuhan City, Hubei Province, Post code: 430072
Deposit date: Sep. 21, 2011
Deposit number: CCTCC No: C201153, hybridoma cell strain 160CT8.3.5.3.2;

China Center for Type Culture Collection
Life Science College of Wuhan university, Luojia Hill, Wuchang, Wuhan City, Hubei Province, China; Post code: 430072
Deposit date: Sep. 21, 2011
Deposit number: CCTCC No: C201154, hybridoma cell strain 160CT8.5.1.1.

Biological deposit Nos. C201153 and C201154 were made in the CCTCC under the conditions of the Budapest Treaty and were viable and capable of reproduction at the time of deposit. Viability tests for deposit Nos. C201153 and C201154 were conducted by the CCTCC on Oct. 28, 2011.

SPECIFIC EMBODIMENTS

The invention is described in detail below in conjunction with the accompanying drawings and the following examples. These examples are only used for the description and not for limiting the scope of the invention.

Example 1

Selection and Preparation of Polypeptide Sequences for Preparation of Anti-Human p28$^{GANK}$ Monoclonal Antibodies 1. Selection of Polypeptide Sequences Based on 226 amino acids sequence information of the p28$^{GANK}$ protein, the following two polypeptide sequences were selected. The design, screening and synthesis were carried out by Pocky Bio-Technology (Shanghai) Co., Ltd:

```
                                              (SEQ ID NO: 1)
NPDAKDHYEATAMHRC (SEQ ID NO: 2)
CDEERVEEAKLLVSQ.
```

2. Synthesis of these Polypeptides

Based on the above-mentioned polypeptide sequence information, the two polypeptides were synthesized by Pocky Bio-Technology (Shanghai) Co., Ltd, 5-10 mg each. The purity of each polypeptide is more than 85%.

Example 2

Preparation and Purification of the Monoclonal Antibodies Against Human p28$^{GANK}$ 1. Synthesis and Coupling of the Antigens According to the sequence disclosed in the GenBank Gene ID: 5716, designed and synthesized the antigen polypeptides. The sequences of the antigen polypeptides were NPDAKDH-YEATAMHRC (SEQ ID NO: 1) CDEERVEEAKLLVSQ (SEQ ID NO: 2), which were synthesized in an automatic synthesizer with solid-phase peptide synthesis technique by Pocky Bio-Technology (Shanghai) Co., Ltd.

Coupling said polypeptide with keyhole limpet hemocyanin (KLH) was performed with the glutaraldehyde linking method described in "Molecular Cloning: A Laboratory Manual", Ed. by J. Sambrook, translated by Jin, Dongyan $2^{th}$ edition, Science Press, 1999, Beijing, p 865".

2. The Preparation and Purification of the Monoclonal Antibodies

100 μg above-mentioned purified polypeptide-KLH conjugate was dissolved in PBS solution, then mixed with an equal volume of Complete Freund's adjuvant (CFA) to develop a uniform emulsion, the latter was used to immunize 5 Balb/c female mice with 5-6 week old; subcutaneous injection in the skin around the two shoulders and intramuscular injection in two legs were performed, about ⅛ of the immunogen used for each injection point; ½ of the remaining immunogen used for intraperitoneal injection. After 1 week, the intraperitoneal booster immunization was performed with 50 μg immunogen and Complete Freund's adjuvant. After 2 weeks, the intraperitoneal booster immunization was performed with 50 μg immunogen and Incomplete Freund's adjuvant (IFA). After 3 weeks, the direct intraperitoneal injection of 50 μg immunogen was performed for weekly booster immunization. From the fifth week, the tail vein blood sample was taken weekly for antibody-titer detection with the following ELISA method: the microtiterplate was coated with 1.25 μg/ml of polypeptide-KLH conjugate-antigen, then blocked with 10% FCS, the diluted serum and then HRP-labeled goat-anti-mouse IgG as the second antibodies were added successively, OPD was finally added to develop the color-reading at 492 nm in a microplate reader (Bio-Rad550 type).

OD values of ELISA obtained by detecting the fourth blood samples were greater than 0.75 at all. $1\times10^6$ cells of SMMC-7721/p28$^{GANK}$ stable cell line transfected with human-p28 GANK gene were lysed with cellular lysis solution for conventional Western Blot test.

The mouse myeloma SP2/0 cells (purchased from ATCC) were prerared at the same time as the immunization of the mice. After 3 days of the last booster immunization, the spleen cells of the mice with the best results in Western Blot and immunohistochemical test were taken to fuse with SP2/0 cells (5:1 ratio) under the effect of PEG 1500; the mixed cells were inoculated into the 96-well microplates, then cultured at 37° C. under 5% $CO_2$ for 14 days. The wells containing grown cell clone were placed under the microscope to detect the fusing-positive cell clone; the calculated total fusion rate was more than 95%. Select the supernatants of the wells containing single cell clone for ELISA detection. The SMMC-7721/p28$^{GANK}$ cells were detected from the ELISA-positive wells using Western Blot and immuno-histochemical test; the obtained cell clones were subcloned twice, western blot and immuno-histochemical test were performed to obtain the best clones. Finally, three clones are obtained.

There are two hybridoma cell strains, one is specific for 160CT8.3.5.3.2 (SEQ ID NO: 1) deposited in the China Center for Type Culture Collection, Deposit date: Sep. 21, 2011, Deposit number: CCTCC No: C201153; the another is specific for 160CT8.5.1.1 (SEQ ID NO: 2) deposited in the China Center for Type Culture Collection, Deposit date: Sep. 21, 2011, Deposit number: CCTCC No: C201154.

6-8 week-old female Balb/c mice were intraperitoneal injected with paraffin oil. After 10 days, intraperitoneal injected $2\times10^6$ hybridoma cells to the mice. The ascites rich in antibodies were extracted from mouse abdominal cavity for detections and purified by the following Protein G affinity chromatography method: the ascites were passed through the protein G affinity chromatography column equilibrated with PBS, then the column was washed with PBS until OD value close to zero, then eluated with 50 nmol/L glycine-HCl solution; the eluents were collected to measure OD value of each collection tube; the eluents with the peak OD value were reserved and purified by dialysis.

Example 3

Identification of Anti-Human p28$^{GANK}$ Monoclonal Antibodies and Their Use in Detection Field 1. The Use of the Monoclonal Antibodies in Western Blot The method is as follows: SDS-PAGE protein electrophoresis of the denatured protein samples were performed, then transferred into a nitrocellulose membrane (Schleicher & Schell company, the membrane was blocked with TBST (containing 5% BSA) for 1 hour, then washed with TBST one time for 5 min, then incubated with p28$^{GANK}$ monoclonal antibodies (as the first antibody, which was diluted with 4% BSA-TBST solution) for 2 hours; washed with TBST solution three times, each for 5 min; then incubated with the IR-800-labeled anti-mouse antibody (as the second antibody, which was diluted with 4% BSA-TBST solution) for 1 hour, further washed with TBST solution for three times, each for 5 min; finally scanned with odyssey infrared laser scanner. The results are shown in FIG. 1 which indicates that these monoclonal antibodies can specifically recognize human p28$^{GANK}$ molecules.

2. The Use of the Monoclonal Antibodies in Immuno-Histochemical Test

Figure 2:
FIG. 2 shows the result of an experiment in which p28$^{GANK}$ proteins in the hepatocarcinoma tissue of one patient with hepatic cancer was detected by a immunohistochemical method using 160CT8531 monoclonal antibody (200×) (A) or 161CT7112 monoclonal antibody (200×) (B).
Figure 2:

The method is as follows: the tissue slices were placed in 60° C. baking oven for 20 min to be dewaxed, then treated with 3% $H_2O_2$ (80% methanol) at room temperature for 10 min to inactivate the endogenous peroxydase; washed with PBS solution three times, each for 5 min; then 0.01 M sodium citrate buffer (pH 6.0) was added to repair the antigen via high pressure; the slices were washed with PBS solution three times, each for 5 min; then blocked with goat serum at room temperature for 20 min; after shaking off excess liquid, the diluted p28$^{GANK}$ monoclonal antibodies (10 µg/ml, as the first antibody) were dropwise added into the slices and incubated at room temperature for 2 hours; washing with PBS three times, each for 5 min; HRP-labeled second antibodies (50 µl) were added into the slices and incubated at room temperature for 1 hour; washing with PBS three times, each for 5 min; DAB was finally added into the slices to develop the color for 5-10 min with control of the staining degree under the microscope; washing with PBS three times, each for 5 min; counterstaining with hematoxylin for 2 min, then differentiating with HCl-alcohol; the slices were rinsed with tap water for 10-15 min; then were dehydrated, transparentized, mounted and photographed. The results are shown in FIG. 2 which indicates that the monoclonal antibodies can more specifically recognize human p28$^{GANK}$ molecules.

3. The Use of the p28$^{GANK}$ Monoclonal Antibodies in the Prognostic Assessment for Hepatocarcinoma Patients 1. Use the tissue microarrays from 200 patients with hepatocarcinoma (Those patients were randomly selected from hepatocarcinoma patients who underwent curative resection in Shanghai Eastern Hepatobiliary Surgery Hospital), the corresponding specimens with perfect history record and follow-up data: enrolled patients' gender, age, tumor size, tumor quadrant, specific pathological subtype, immuno-histochemical results, lymph node metastasis, portal vein cancer-thrombosis, intrahepatic vascular invasion, etc. The postoperative disease-free survival time (DFS), overall survival time (OS) and recurrence metastasis was also recorded.

Figure 3:
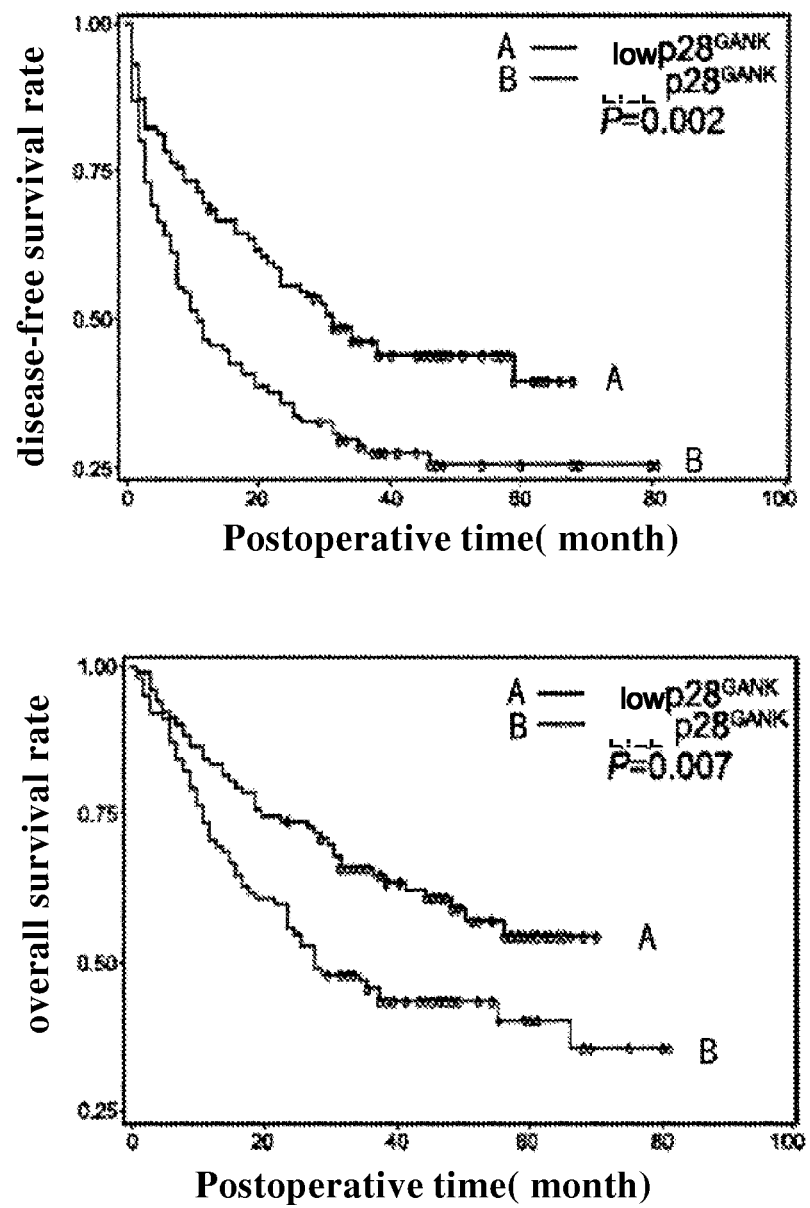
FIG. 3 shows a result of an experiment in which p28$^{GANK}$ proteins in the hepatocarcinoma tissues of 200 patients with hepatocarcinoma was detected by a immunohistochemical method using 161CT7112 monoclonal antibody. The disease-free and overall survival rates of 200 patients with HCC were compared between the low-p28$^{GANK}$ (A: below the median value) and high-p28$^{GANK}$ expression (B: above the median value) samples are shown.

2. The monoclonal antibodies were used to detect and assess the p28$^{GANK}$ expression: the p28$^{GANK}$ expression in tissue microarray arrays was detected, the density of positive p28$^{GANK}$ staining was measured with the use of a computerized image system (Leica Microsystems Imaging Solutions Ltd, Cambridge, United Kingdom). The density was counted by Image-Pro Plus v6.2 software (Media Cybernetics Inc, Bethesda, Md.). Integrated optical density of all the positive staining in each photograph was measured, and its ratio to total area of each photograph was calculated as density. The relationship between the p28$^{GANK}$ expression and various clinical features and the prognostic parameters (overall survival rate, disease-free survival rate, OS, DFS, etc.) were analyzed using statistical software, their graphs were obtained. The results are shown in FIG. 3, which indicates that the density of p28$^{GANK}$ expression correlates to clinical parameters and the significance for poor prognosis. Therefore, it indicates that the antibodies of the present invention can be used to determine the prognostic assessment of patients with HCC.

What is claimed is:

1. A monoclonal antibody against human p28$^{GANK}$ produced by a hybridoma cell strain having CCTCC Deposit No: C201153 or CCTCC Deposit No: C201154.

2. A hybridoma cell strain having CCTCC Deposit No: C201153 or CCTCC Deposit No: C201154.

3. A method for preparation of monoclonal antibody against human p28$^{GANK}$, comprising the following steps:
   a) synthesizing a polypeptide comprising the amino acid sequence as shown in SEQ ID NO:1 or SEQ ID NO:2;
   b) coupling the above-mentioned polypeptide with keyhole limpet hemocyanin to produce an immunogen, which is used to immunize mice;
   c) obtaining the spleen cells of the immunized mice, and fusing the spleen cells with mouse myeloma cells;
   d) obtaining positive cell clones which can react with the synthesized polypeptide through multiple rounds of screening, said cell clones are used as hybridoma cell strains which can secrete the monoclonal antibodies against human p28$^{GANK}$, the deposit number of said hybridoma cell strain is CCTCC Deposit No: C201153 or CCTCC Deposit No: C201154;
   e) inoculating the hybridoma cell strain to the mice and obtained the ascite (including antibody), purify the ascite to obtain the monoclonal antibody against human p28$^{GANK}$; or, culture said hybridoma cells in vitro, then isolate and purify the culture product to obtain the monoclonal antibody against human p28$^{GANK}$.

4. A method of preparing the monoclonal antibody of claim 1, comprising using a polypeptide comprising the amino acid sequence as shown in SEQ ID NO: 1 or SEQ ID NO: 2 to produce a monoclonal antibody against human p28$^{GANK}$.

5. A method of preparing the hybridoma cell strain of claim 2, comprising using a polypeptide comprising the amino acid sequence as shown in SEQ ID NO: 1 or SEQ ID NO: 2 to produce a hybridoma cell strain.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 1

Asn Pro Asp Ala Lys Asp His Tyr Glu Ala Thr Ala Met His Arg Cys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 2

Cys Asp Glu Glu Arg Val Glu Glu Ala Lys Leu Leu Val Ser Gln
1               5                   10                  15
```